United States Patent
Herrera Sanchez et al.

(10) Patent No.: US 9,334,479 B2
(45) Date of Patent: May 10, 2016

(54) LIVER PROGENITOR CELLS

(75) Inventors: Maria Beatriz Herrera Sanchez, Turin (IT); Benedetta Bussolati, Moncalieri (IT); Giovanni Camussi, Turin (IT); Stefano Buttiglieri, Chieri (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1707 days.

(21) Appl. No.: 11/921,030

(22) PCT Filed: May 24, 2006

(86) PCT No.: PCT/IT2006/000391
§ 371 (c)(1),
(2), (4) Date: Nov. 26, 2007

(87) PCT Pub. No.: WO2006/126236
PCT Pub. Date: Nov. 30, 2006

(65) Prior Publication Data
US 2010/0003752 A1 Jan. 7, 2010

(30) Foreign Application Priority Data

May 26, 2005 (WO) .................. PCT/IT2005/000303

(51) Int. Cl.
*C12N 5/071* (2010.01)
*A61K 35/12* (2015.01)

(52) U.S. Cl.
CPC .............. *C12N 5/067* (2013.01); *C12N 5/0672* (2013.01); *A61K 35/12* (2013.01); *C12N 2510/02* (2013.01)

(58) Field of Classification Search
None
See application file for complete search history.

(56) References Cited

U.S. PATENT DOCUMENTS

| 2003/0138951 | A1 | 7/2003 | Yin | |
| 2005/0074876 | A1 | 4/2005 | Strick-Marchand et al. | |
| 2009/0053758 | A1* | 2/2009 | Kubota et al. | 435/32 |
| 2010/0093090 | A1* | 4/2010 | Deng et al. | 435/377 |

FOREIGN PATENT DOCUMENTS

| EP | 1 394 263 A1 | 3/2004 |
| WO | WO 00/03001 | 1/2000 |
| WO | WO 00/43498 A3 | 7/2000 |
| WO | WO 03/078588 A2 | 9/2003 |

OTHER PUBLICATIONS

Malhi, H., et al., "Isolation of Human Progenitor Liver Epithelial Cells with Extensive Replication Capacity and Differentiation into Mature Hepatocytes," Journal of Cell Science, vol. 115, No. 13, pp. 2679-2688, Jul. 1, 2002.
Suzuki, A., et al., "Flow-Cytometric Separation and Enrichment of Hepatic Progenitor Cells in the Developing Mouse Liver," Hepatology, vol. 32, No. 6, pp. 1230-1239, Dec. 6, 2000.
Yang L., et al., "In vitro Trans-Differentiation of Adult Hepatic Stem Cells into Pancreatic Endocrine Hormone-Producing Cells," Proceedings of the National Academy of Sciences of the U.S.A. vol. 99, No. 12, pp. 8078-8083, Jun. 11, 2002.
Schwartz, R.E., et al., "Multipotent Adult Progenitor Cells from Bone Marrow Differentiate into Functional Hepatocyte-like Cells," Journal of Clinical Investigation, vol. 109, No. 10, pp. 1291-1302, May 2002.
Suzuki, A., et al., "Clonal Identification and Characterization of Self-Renewing Pluripotent Stem Cells in the Developing Liver," Journal of Cell Biology, vol. 156, No. 1, pp. 173-184, Jan. 7, 2002.
Forbes S., et al., "Hepatic Stem Cells," Journal of Pathology, vol. 197, No. 4, pp. 510-518, May 30, 2002.
Petersen, B.E., et al., "Hepatic Oval Cells Express Stem Cell Markers Thy-1 in the Rat," Heptalogy, vol. 27, No. 2, pp. 433-445, Feb. 1998.
Petersen, B.E., et al., "Mouse A6-Positive Hepatic Oval Cells Also Express Several Hematopoietic Stem Cell Markers," Heptalogy, vol. 37, No. 3, pp. 632-640, Mar. 2003.
Mitaka, T., "Reconstruction of Hepatic Organoid by Hepatic Stem Cells," Journal of HBP Surgery, pp. 697-703, 2002.
Hillen, W., et al., "Control of Expression of the Tn10-encoded Tetracycline Resistence Genes," Journal of Mol. Biology, vol. 169, pp. 707-721, 1983.
Hillen, W., et al., "Analysis of tet Operator-TET Repressor Complexes by Thermal Denaturation Studies," Nucleic Acids Research, vol. 10, No. 19, pp. 6085-6097, 1982.
Hillen, W., et al., "Mechanisms Underlying Expression of Tn10 Encoded Tetracycline Resistance," Microbology, pp. 345-369, 1994.

* cited by examiner

*Primary Examiner* — Catherine S Hibbert
(74) *Attorney, Agent, or Firm* — Jacobson Holman, PLLC.

(57) ABSTRACT

The invention relates to human liver pluripotent progenitor cell lines which express hepatic cell markers such as albumin and α-fetoprotein and do not express some of the markers which are typical of oval stem cells. Also disclosed is a method of isolating the cell lines of the invention, methods for differentiating said cells into a plurality of different cell lineages, methods for conditional immortalization and metabolic selection of said cells, as well as the use of the cell lines of the invention for preparing a medicament with osteogenic differentiation activity or liver injury regeneration activity.

18 Claims, 2 Drawing Sheets

LIVER PROGENITOR CELLS

The present invention relates to a method of isolating progenitor cells from adult liver tissue, liver progenitor cells isolated by the method of the invention, as well as methods of inducing differentiation of the isolated liver progenitor cells and methods of conditional immortalization and metabolic selection of the liver progenitor cells. More specifically, the invention relates to liver progenitor cells which, although being liver-derived, are morphologically different from hepatic oval stem cells and do not express markers which are typical of hepatic oval stem cells. Additionally, the liver progenitor cells of the invention show self-renewing capability and multilineage differentiation potential, which features allow to categorize these cells as pluripotent progenitor cells.

Liver stem cells, including human liver stem cells, are disclosed in the prior art, for example in WO 03/078588, WO 00/43498, WO 00/03001, EP 1394263, US 2003/0138951. Most known liver stem cells are designated as hepatic oval stem cells, due to their characteristic oval shape. Oval stem cells are a well defined type of liver stem cells. Typical features thereof are, besides their characteristic oval morphology, the expression of one or more surface markers which are typical of hematopoietic stem cells, such as c-kit (CD117), CD34 and Sca-1, suggesting that oval stem cells originate from hematopoietic stem cells. Furthermore, oval stem cells are bipotent progenitors capable of generating both hepatocytes and cholangiocytes in vivo (Petersen B. E., Goff J. P., Greenberger J. S., Michalopoulos G. K. (1998) Rat oval cells express the hematopoietic stem cell marker Thy-1 in the rat. Hepatology 27, 433-445; Petersen B. E., Grossbard B., Hatch H., Pi L., Deng J., Scott E. W. (2003) Mouse A6-positive hepatic oval cells also express several hematopoietic stem cell markers. Hepatology 37, 632-640).

The present inventors have now surprisingly found a method of isolating progenitor cells from adult liver tissue which results in the isolation of a novel progenitor cell population which is characterized either by the expression of some cell markers which are typical of hepatic cells, such as albumin and α-fetoprotein, and by the absence of morphological and molecular features typical of oval stem cells. The novel liver progenitor cells of the invention are in fact epithelioid in shape rather than being oval-shaped. Moreover, such cells do not appear to express some of the hemopoietic cell markers which are typical of hepatic oval stem cells.

Figure 1:
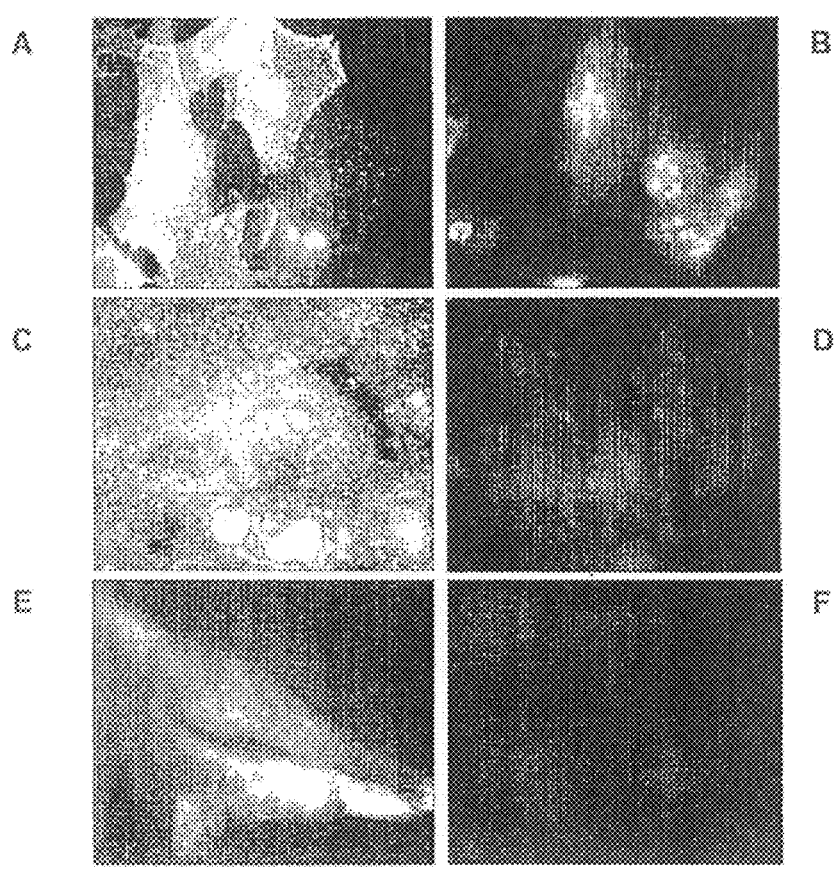
FIG. 1 contains microscopic photographs showing cells obtained in accordance with the instant invention and their respective isotypic negative controls.

Accordingly, in a first aspect, the present invention provides a method of isolating a non-oval human liver progenitor cell line expressing hepatic cell markers, preferably albumin and α-fetoprotein, said cell line preferably not expressing hemopoietic cell markers, the method comprising the steps of:
(i) culturing adult liver-derived human mature hepatocytes in a cell culture medium until death of mature hepatocytes and selection of a population of surviving cells having epithelioid morphology;
(ii) expanding the population of surviving cells by culturing in a serum-containing, glucose-containing culture medium supplemented with hEGF (human epithelial growth factor) and bFGF (basic fibroblast growth factor) and comprising usual inorganic salts, amino acids and vitamins necessary for the growth of mammalian cells.

The mature hepatocyes employed in the method of the invention are obtained from adult liver tissue according to any procedure known per se for the isolation of hepatocytes from mammalian liver, preferably human liver. The meaning of the expression "adult liver tissue" as used herein is well-established in the prior art and it means liver tissue obtained from a postnatal organism. The meaning of the expression "mature hepatocytes" is also well-established in the prior art. This expression encompasses completely differentiated hepatocytes which do not have the ability to proliferate in vitro. Commonly used differentiation markers for mature hepatocytes are biochemical markers, such as albumin, tyrosine aminotransferase (TAT), cytochrome P450, TO, serine dehydratase (SDH), Cxs 32 and 26, as well as morphologycal markers, such as bile-canaliculus formation, gap-junctions, peroxisomes with crystalline nucleoids a high number of mitochondria (see for example Mitaka T (2002). Reconstruction of hepatic organoid by hepatic stem cells. J Hepatobiliary Pancreat Surg.; 9(6):697-703).

The mature hepatocytes may optionally be frozen in a serum-containing culture medium in the presence of a cryoprotecting agent prior to culturing. The hepatocytes are preferably frozen in a liquid medium comprising 20% of heat inactivated fetal calf serum (FCS) or human serum (HS) and containing dimethyl sulfoxide (DMSO) as the cryoprotecting agent. Alternatively, any other compound known to possess cryoprotecting properties may be used as the cryoprotecting agent, such as for example glycerol, ethylene glycol, polyethylene glycol, or polyvinylpyrrolidone. Freezing is preferably carried out at very low temperatures, for example by placing the cells sample at −80° C. and subsequently in liquid nitrogen.

The isolation method of the invention comprises a first step in which the primary culture of mature hepatocytes is subjected to negative selection and a second step in which the population of surviving cells is expanded.

In the first step, the hepatocytes are cultured in stringent conditions until death of the primary culture of mature hepatocytes is induced. For this purpose, the hepatocytes may be seeded at a density of about $1.0$-$1.5 \times 10^5$ viable cells per $cm^2$ onto collagen-coated culture plates and cultured in an Hepatocyte Cell Culture Medium for about at least 2 weeks. After about 2 weeks, the large majority of hepatocytes die but a population of cluster-forming cells survives. Such cluster-forming cells are readily distinguishable from mature hepatocytes by their epithelioid morphology.

In the second step, the clusters of surviving cells are removed, plated in limiting dilution and cultured in a serum-containing, glucose-containing rich culture medium supplemented with hEGF and bFGF, which medium being capable of sustaining the growth of the cell clusters. The concentration of hEGF in the rich medium is preferably comprised between 2 and 10 ng/ml; the concentration of bFGF is preferably comprised between 10 and 50 μg/ml. More preferably, the rich culture medium used in the expansion step is a mixture of alpha Minimal Essential Medium (αMEM) and Endothelial Basal Medium (EBM) (3:1 vol/vol), supplemented with FCS and/or HS, glutamine and antibiotics. Endothelial Basal Medium (EBM) comprises suitable concentrations of the growth factors hEGF and bFGF. A buffering agent may be added to the rich medium in order to maintain pH at about neutral values (preferably, pH 7.4). The appearance of individual attached colonies is observed after about 3 weeks in culture. Single clones are subcultured, expanded and analysed when they approach confluence.

The human liver progenitor cells obtained by the above described method are unable to grow in αMEM supplemented with 10% FCS and 10% HS, which is the commonly used culture medium for mesenchymal stem cells.

Twenty four different cell clones were obtained by the above-described method. The clones were kept in culture in undifferentiating medium for 2-3 months. Around 200 million cells were generated from a single clone, indicating a life span of obtained 200-250 doublings. These data indicate that the liver-derived progenitor cells of the invention are capable of self-renewing.

According to a preferred embodiment of the method of the invention, the cells having epithelioid morphology obtained in step (ii) may optionally be subjected to conditional immortalization and metabolic selection.

Conditional immortalization provides immortalized cell lines with stable metabolic functions. Conditional immortalization may be achieved for example by subcloning the Large T antigen from SV40 or any other gene having the activity of inducing or maintaining the entry into the cell cycle, such as e.g. Bmi-1, h-TERT or c-Myc, into a non-viral vector such as pcDNA4/TO (Invitrogen) which includes the regulatory elements from the *E. coli* Tn10-encoded tetracycline (Tet) resistance operon (Hillen and Berens, 1994; Hillen et al., 1983). The addition of a second regulatory vector such as pcDNA6/TR (Invitrogen) which expresses high levels of the TetR gene, induces the expression of the immortalizing gene and controlled cell growth.

The immortalized cells are then subjected to metabolic selection by replacing glucose in the cell culture medium with galactose which is metabolised by hepatic cells only.

Another aspect of the present invention are the liver-derived cells obtained as described above. Such cells have been shown to differentiate under suitable culture conditions into mature hepatocytes or insulin-producing cells, marking these cells as liver progenitor cells. Additionally, the cell lines of the invention have been shown to undergo osteogenic and endothelial differentiation when cultured in the appropriate differentiation media. Moreover, the cell lines of the invention are characterized by a unique cell marker expression profile which, to the Applicant's knowledge, has never been disclosed so far and which is different from the expression profile of liver oval stem cells, suggesting that a novel cell type has been identified.

Characterization by FACS (Fluorescence Activated Cell Sorting), Immunofluorescence and RT-PCR of the expression profile of a number of cell markers of the liver-derived human progenitor cell lines of the invention shows the presence of several stem cell markers and liver tissue-specific markers. The following cell antigens were tested: CD34, C-kit, SCA-1, CD29, CD73, CD45, CD133, CD146, CD105, CD44, CD90, CD117, CD14, HLA-A, B, C, α-fetoprotein, Cytokeratin 19, Albumin and Cytokeratin 18. The results are summarized in table I below.

TABLE I

| Marker | FACS analysis of HuHEP clones (% of positive cells: mean ± SD) |
|---|---|
| CD34 | − |
| CD45 | − |
| CD14 | − |
| CD73 | + |
| CD29 | + |
| CD44 | + |

TABLE I-continued

| | |
|---|---|
| CD117 (c-Kit) | − |
| CD90 (Thy-1) | + |
| CD146 | − |
| CD133 | − |
| CD105 (endoglin) | + |

| Marker | Immunofluorescence anaysis of HuHEP clones (% of positive cells: mean ± SD) |
|---|---|
| α-fetoprotein (AFP) | + |
| CK18 | + |
| CK19 | − |
| Albumin(ALB) | + |
| HLA-A, B, C | + |

The results indicate that the liver-derived human progenitor cells of the invention express markers of both stem cells and liver cells, thereby confirming that such cells are liver precursors. Particularly, FIG. 1 shows that the non-oval liver human progenitor cells obtained (referred to in Table 1 and in the following as "HuHEP") express albumin (A), α-fetoprotein (C) and Cytokeratin 18 (E) as detected by immunofluorescence using specific antibodies. B, D, F are the respective isotypic negative controls. (×400).

The expression of albumin, α-fetoprotein and cytokeratin 18 is typical of hepatic cells and characterizes the cell lines of the invention as liver progenitor cells, in the absence of typical mature liver cell markers such as cytochrome P450 and the ability to synthesize urea.

The morphology and the surface markers detected and listed in Table I above, characterize a population which is different from hepatic oval stem cells. Particularly, the cell lines of the invention do not express CD-117 (C-kit) nor CK19 (Cytokeratin 19), which are typical markers of oval stem cells. Another typical marker of oval stem cells, i.e. CD34, is also absent from the cell lines of the invention.

Furthermore, the cell lines of the invention do not express cell surface markers which are typical of hematopoietic stem cells (such as CD117, CD34, CD45 and CD133) contrary to other liver stem cells such as the human primitive hepatic stem cells described in WO 03/078588 and the oval stem cells. On the other hand, the cell lines of the invention express several cell surface markers which are typical of other stem cells, for example CD29, CD73, CD146, CD105 (endoglin), CD44, CD90 (Thy-1) and HLA-A, B, C.

An extremely advantageous feature of the progenitor cell lines of the invention is that they are capable of differentiating into a plurality of different cell lineages. Particularly, the progenitor cell lines of the invention are capable of differentiating into mature liver cells, insulin-producing cells, osteogenic cells and endothelial cells when cultured under suitable differentiation conditions.

For differentiation into mature liver cells, the cells of the invention are cultured in a serum-containing culture medium, preferably MEM-EBM (3:1)+10% FCS and/or HS, supplemented with hepatocyte growth factor (HGF) and fibroblast growth factor 4 (FGF-4).

For differentiation into insulin-producing cells, the cells of the invention are cultured in a serum-containing culture medium, preferably DMEM supplemented with 2% FCS and/or HS, in the presence of at least 2 g/l glucose, preferably 4.5 g/l glucose. More preferably, nicotinamide is added to the serum-containing culture medium after about 1 month of culture in the presence of glucose. A suitable concentration for nicotinamide in the culture medium is about 10 mM.

For osteogenic differentiation, the cells of the invention are cultured in a serum-containing culture medium, preferably αMEM, supplemented with ascorbate-2-phospate and dexamethasone with inorganic phosphate.

For endothelial differentiation, the cells of the invention are cultured in an endothelial cell basal medium, preferably EBM-2, supplemented with VEGF (Vascular Endothelial Growth Factor).

The non-oval liver progenitor cells of the invention were inoculated subcoutaneously into SCID mice to evaluate the appearance of tumors. No tumor was observed after six months. Since, as mentioned above, the non-oval liver progenitor cell lines of the invention can be expanded, maintained in culture for several passages, cryopreserved and differentiated, and also in the light of their differentiating properties, such cells are useful in a number of applications including, inter alia, the use as a substrate for cultures of hepatitis viruses, the use as an in vitro model for drug-testing, the application in regenerative therapy and the application in the development of a bioartificial liver.

The following examples are provided by way of illustration only and are not intended to limit the scope of the invention as determined by the appended claims.

EXAMPLES

Cryopreservation

Normal human mature hepatocytes obtained from adult human liver tissue were cryopreserved in heat inactivated Fetal Calf Serum (FCS) supplemented with 10% of filter-sterilized dimethyl sulfoxide (DMSO) and the vials were stored in liquid nitrogen. The hepatocytes were thawed to control cell viability after freezing, by determining the number of viable cells by dye exclusion assay using the dye Trypan blue. Experiments showed that cell viability was >90% and that the thawed cells maintained their phenotype and differentiating capabilities.

Isolation and Culture of Non-Oval Human Liver Progenitor Cells (HuHEP)

Hepatocytes were obtained from 8 different normal human liver preparations, including 2 preparations from fresh liver and 6 preparations of cryopreserved hepatocytes (obtained from Cambrex (Bio Science, Verviers, Belgium, ULB: cambrex.com).

Preparation from Fresh Liver Tissue

Human hepatocytes were isolated from fresh surgical specimens of patients undergoing hepatectomy. Healthy liver tissue (5-20 g) was used to isolate hepatocytes by collagenase digestion. Briefly, livers tissues were isolated and perfused with 350 ml of warm (37° C.) Ca-free buffer (Liver Perfusion Medium, GIBCO, Grand Island, N.Y.; ULB: invitrogen-.com). Then the liver tissues were digested in Liver Digest Medium (GIBCO) at 37° C. This resulted in blanching, softening and dissociation of the liver tissue and provided complete digestion of the liver within 10-12 min. The hepatocytes were released by mincing and pipetting with a large bore pipette. The cell suspension was filtered through a sterile 100 μm nylon mesh into a beaker placed on ice, sedimented by centrifugation at 50 g for 5 min, resuspended and washed 2-3 times in cold wash medium (Hepatocyte Wash Medium, GIBCO).

Negative Selection

The hepatocytes obtained as described above were initially plated on Williams Medium E medium (GIBCO) further supplemented with glutamine and with 5% fetal calf serum (FCS, Euroclone, Wetherby, UK, ULB: euroclone.net). Unattached cells were poured off 2 to 3 h later and then replaced with hepatocyte serum-free medium (Hepatozyme-SFM, GIBCO), a highly modified Chees' Medium supplemented with 1.25 μg/cm$^2$ collagen to provide a sandwich matrix. Cultures were re-fed with Hepatozyme SFM (without collagen) at 24 h and every 48 h thereafter. The hepatocytes were seeded at a density of 1.0-1.5×10$^5$ viable cells [80% viable cells determined by the trypan blue (GIBCO)] per cm$^2$ onto collagen-coated culture plates in Hepatozyme-SFM maintained at 37° C., 5% $CO_2$ for 2 weeks. After about 2 weeks in culture, extensive death of hepatocytes was observed.

Expansion

The culture medium was substituted with alfa-Minimum Essential Medium/Endothelial Cell Basal Medium-1 (αMEM/EBM) (3:1) (GIBCO/Cambrex supplemented with L-glutamine (5 mM), Hepes (12 mM, pH 7.4), penicillin (50 IU/ml), streptomycin (50 μg/ml) (all from Sigma-Aldrich, St. Louis, Mo.; ULB: sigmaaldrich.com), FCS (10%) and Horse serum (10%, HS, GIBCO. Individual attached cells were identified on the culture dish after another 3 weeks. When colonies were evident, cloning rings were placed around them, and they were subcultured to an individual well of a 24-well culture plate. The expanded cells were transferred to a 75-cm$^2$ flask and analyzed when they approached confluence.

Cryopreserved Hepatocytes

Human cryopreserved normal hepatocytes were cultured under the same culture conditions (negative selection and expansion) as described above, providing similar results.

Conditional Immortalization

Cells cultured for about 10 passages were detached and subjected to electroporation at 180 V for 20 msec with 5 μg of vector pcDNA4/TO (Invitrogen) bearing the subcloned large T antigen from SV40. The cells were selected with zeocin (5 μg/ml) for 3 weeks.

The cells were then subjected to a second electroporation at 180 V for 20 msec with 5 μg of vector pcDNA6/TR (Invitrogen) and selected for 3 weeks with blasticidin (5 μg/ml) in the presence of doxycycline (1 μg/ml). The cells were feeded every 3 days in DMEM medium (DMEM: Dulbecco's MEM) supplemented with 10% FCS in the presence of doxycycline (1 μg/ml).

Metabolic Selection

The immortalized cells obtained as described above induced to growth with doxycycline (1 μg/ml) were cultured in glucose-free RPMI medium comprising 1 μg/ml galactose and 3% FCS for 30 days, in order to select the cells which are specifically capable of using galactose instead of glucose, which is a typical feature of hepatic cells. The cells were tested and cryopreserved.

Differentiation of HuHEP in Hepatocytes and Insulin-Producing Cells

In order to verify if the HuHep cells were capable of differentiating into mature hepatocytes, the expression of cytochrome P450, i.e. the metabolic oxidation enzyme, under different culture conditions was evaluated. The cells were cultured for 15 days in the following culture conditions:

HuHEP were cultured in a bioreactor with MEM/EBM medium supplemented with 10% FCS/HS+HGF/FGF-4. After 15 days of culture cytochrome P450-positive HuHEP were evaluated. 20-25% of the total population of HuHEP cultured in MEM/EBM+10% FCS+HGF/FGF-4 was cytochrome P450-positive. Urea concentration was in the range 3-4 mg/dL, glucose was a half of the total glucose initially present in the fresh medium, and there was no modification of total protein, indicating that the differentiated hepatocytes were metabolically active.

Figure 2:
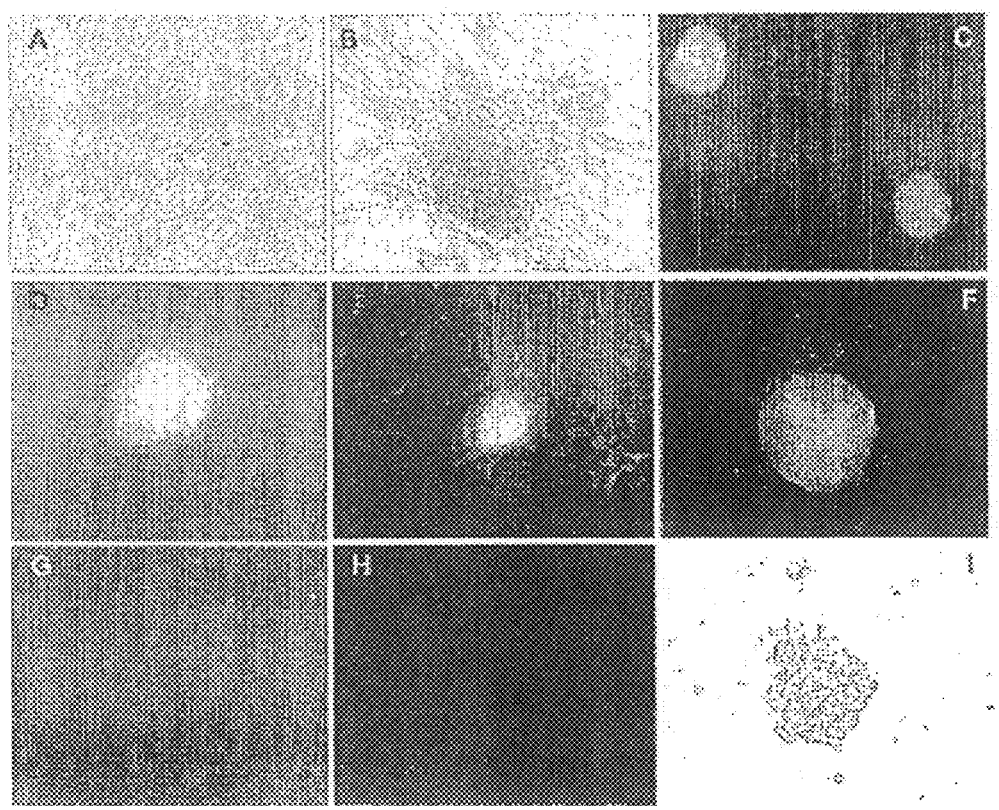
FIG. 2 contains microscopic photographs showing test results using cells obtained in accordance with the instant invention and their respective isotypic negative controls.

Furthermore, HuHEP were differentiated into insulin-producing cells with incubation in DMEM medium (DMEM:

Dulbecco's MEM) supplemented with 2% FCS/HS and a high glucose content (at least 2 g/l glucose, preferably 4.5 g/l glucose) for 1 month, and optionally for 5-7 days in the presence of 10 mM nicotinamide. Cells began to form small spheroid cell clusters on top of the confluent cell monolayer which morphologically resembled pancreatic islets. This three-dimensional cell clusters positively stained with the polyclonal antibody against human insulin and the monoclonal antibody against human Glucose transporter Type 2 (Glut2) which is a glucose transporter (FIG. 2). Moreover, the three-dimensional cell clusters stained with the Zn-chelating agent dithizone, which is specific for the insulin containing granules. These results are shown in FIG. 2, which shows the morphological appearance of unstimulated HuHEP (panel A), HuHEP stimulated with the differentiating medium that induces pancreatic islet-like structures formation (panel B). FIG. 2, panels C and D: immunofluorescence staining for human insulin; panels E and F: immunofluorescence staining for human Glut2; panels G and H: staining with negative isotypic controls; panel I: staining with the Zn-chelating agent dithizone. (A, B, D, F, G, H, I×250; C and E×150).

In Vitro Osteogenic Differentiation

To induce osteogenic differentiation, the cells were cultured in αMEM supplemented with 10% FCS, 10% HS, 100 U/mL penicillin, 100 µg/mL streptomycin, 12 mM L-glutamine, 20 mM β-glycerol phosphate, 50 ng/mL thyroxine, 1 nM dexamethasone, and 0.5 µM ascorbate 2-phosphate (all from Sigma-Aldrich). The medium was replaced with fresh medium twice a week for 3 weeks. To evaluate differentiation, the cells were fixed with 4% paraformaldehyde for 20 minutes at RT and stained with Alizarin Red, pH 4.1 (Sigma) for 20 minutes at RT.

The cells cultured for 3 weeks in osteogenic differentiation medium exhibited deposits of calcium and expression of osteocalcin and osteopontin, indicating osteogenic differentiation. Moreover, the cells became negative for albumin, AFP and CK18.

After 6 weeks in the same medium but without inorganic phosphate, lipid accumulation was not detected.

In Vitro Endothelial Differentiation

Endothelial cell differentiation was obtained by culturing the cells in EBM-2 medium (Cambrex) for 10 days with Vascular Endothelial Growth Factor (VEGF, 10 ng/ml, Sigma). When cultured in EBM supplemented with VEGF, the cells expressed the endothelial markers CD31, CD34, KDR (VEGFR-2), CD144 (VE-cadherin), and von Willebrand factor that were negative in undifferentiated conditions, indicating an endothelial differentiation. During endothelial differentiation albumin, AFP and CK18 were lost.

Effects of HuHEP Injection in Acetaminophen-Induced Liver Injury in SCID

Acetaminophen hepatoxicity is a well recognized model of hepatic necrosis. The increased levels of N-acetyl-p-benzoquinone imine (NAPQI), the toxic metabolite of acetaminophen, are responsible for hepatic necrosis.

Animal Model and HuHEP Transplantation

SCID mice were from Charles River (Jackson Laboratories, Bar Harbor, Me.). They were housed in a specific pathogen-free environment. Male SCID mice 8 weeks old were used for the experiments. The experiments were performed in accordance with the guidelines of the National Institute of Health. After a 16-hour fast, the mice were injected intraperitoneally with 250 mg/kg acetaminophen (Sigma, St. Louis, Mo.) dissolved in sterile saline or sterile saline alone as the vehicle control. After injection with acetaminophen, mice were fed ad libitum with standard chow.

The peak of liver injury was observed 1 day after acetaminophen injection. At this time, HuHEP (passage III-IV) were harvested using trypsin-EDTA, washed with PBS, labeled with the PKH26 red fluorescent cell linker kit (Sigma) counted in a microcytometer chamber and resuspended in PBS ($1 \times 10^6$ in 250 µl PBS).

Plasma Aminotransferase Measurements

Plasma or serum levels of aspartate aminotransferase (AST) and alanine aminotransferase (ALT) were measured at 37° C. with a commercially available kit (Sigma Diagnostic).

Histology

Hepatic tissue was formalin fixed and paraffin embedded before sectioning. Liver sections were stained with hemotoxylin-eosin.

For cryostatic preservation, hepatic tissues were maintained in 4% formaldehyde solution overnight. The next day formaldehyde was removed and replaced by 70% EtOH. Then the tissues were fixed in OCT.

Quantitative analysis of the extent of tissue necrosis was performed after digitally imaging three high-power fields per slide in a random and blinded fashion. Areas of tissue necrosis or impending necrosis were identified according to the presence of decreased eosinophilia, loss of cell architecture, vacuolization, cell disruption, or karyolysis.

Immunofluorescence

Cryostatic liver sections were incubated with FITC-conjugated mouse anti-human HLA-A, B, C monoclonal Antibody (BioLegend, San Diego, Calif.) (1:200), or with the control mouse monoclonal $IgG_1$, for 1 hour at room temperature. Three non-sequential sections were examined for each specimen.

Results of In Vivo Experiments

Acetaminophen induced extensive necrotic injury of the liver. The injection of labelled HuHEP 24 hours after induction of hepatic injury resulted in local recruitment of HuHEP at the site of the liver injury. The cells were found to contribute to liver regeneration as they are detectable in the liver of SCID mice 15 days after liver injury.

The above in vitro and in vivo experimental results indicate that the non-oval human liver progenitor cell lines of the present invention are suitable for use for preparing a medicament having osteogenic differentiation activity as well as a medicament having liver injury regeneration activity.

The invention claimed is:

1. An expanded non-oval human liver pluripotent progenitor cell line isolated from adult tissue which expresses the hepatic cell marker albumin and the stem cell markers CD44, CD73, and CD90, which does not express the cell markers CD117, CD34, and CD45, and which is capable of differentiating into mature liver cells.

2. The isolated expanded cell line according to claim 1, which further expresses the hepatic cell marker α-fetoprotein.

3. The isolated expanded cell line according to claim 1, which further expresses the hepatic cell marker CK18.

4. The isolated expanded cell line according to claim 1, which further expresses the stem cell markers CD29, CD146, and CD105.

5. The isolated expanded cell line according to claim 1, which further does not express hemopoietic cell markers.

6. The isolated expanded cell line according to claim 1, which further does not express the hematopoietic stem cell marker CD133.

7. The isolated expanded cell line according to claim 1, which further does not express the oval cell marker CD19.

8. The isolated expanded cell line according to claim 1, which further does not express the mature hepatocyte cell marker cytochrome P450 and does not synthesize urea.

9. A method of differentiating the isolated expanded non-oval human liver pluripotent progenitor cell line according to claim 1 into mature liver cells capable of expressing the mature hepatocyte cell marker cytochrome P450 and capable of synthesizing urea, comprising culturing said cell line in a serum-containing culture medium supplemented with hepatocyte growth factor (HGF) and fibroblast growth factor 4 (FGF-4).

10. The method according to claim 9, wherein said serum-containing culture medium is MEM-EBM supplemented with 10% FCS or HS, HGF and FGF-4.

11. The method according to claim 9, wherein said non-oval human liver pluripotent progenitor cell line is cultured in a bioreactor.

12. A method of differentiating the isolated expanded non-oval human liver pluripotent progenitor cell line according to claim 1 into insulin-producing cells, comprising culturing said cell line in a serum-containing culture medium in the presence of at least 2 g/l glucose.

13. The method according to claim 12, wherein the serum-containing culture medium further comprises nicotinamide.

14. The method according to claim 12, wherein the serum-containing culture medium is DMEM supplemented with 2% FCS or HS, 4.5 g/l glucose and 10 mM nicotinamide.

15. A method of differentiating the isolated expanded non-oval human liver pluripotent progenitor cell line according to claim 1 into osteogenic cells, comprising culturing said cell line in a serum-containing culture medium supplemented with ascorbate-2-phosphate and dexamethasone with inorganic phosphate.

16. The method according to claim 15, wherein the serum-containing culture medium is αMEM supplemented with 10% FCS, 10% HS, 1 nM dexamethasone and 0.5 μM ascorbate 2-phosphate.

17. A method of differentiating the isolated expanded non oval human liver pluripotent progenitor cell line according to claim 1 into endothelial cells, comprising culturing said cell line in an endothelial cell basal medium supplemented with vascular endothelial growth factor (VEGF).

18. The method according to claim 17, wherein the endothelial cell basal medium is EBM-2 supplemented with 10 ng/ml VEGF.

* * * * *

UNITED STATES PATENT AND TRADEMARK OFFICE
CERTIFICATE OF CORRECTION

PATENT NO. : 9,334,479 B2
APPLICATION NO. : 11/921030
DATED : May 10, 2016
INVENTOR(S) : Herrera Sanchez et al.

Page 1 of 1

It is certified that error appears in the above-identified patent and that said Letters Patent is hereby corrected as shown below:

In the claims:

In claim 7, column 8, line 67, please change "cell marker CD19." to --cell marker CK19.--

Signed and Sealed this
Ninth Day of August, 2016

Michelle K. Lee
*Director of the United States Patent and Trademark Office*